(12) United States Patent
Lu et al.

(10) Patent No.: US 9,624,179 B1
(45) Date of Patent: Apr. 18, 2017

(54) QUINAZOLINE DERIVATIVE LU1501 AND PREPARING METHOD AND APPLICATION THEREOF

(71) Applicant: NANJING GENERAL HOSPITAL OF NANJING MILITARY REGION OF PLA, Nanjing, Jiangsu (CN)

(72) Inventors: Guangming Lu, Jiangsu (CN); Zhuoli Zhang, Jiangsu (CN); Jing Pan, Jiangsu (CN)

(73) Assignee: NANJING GENERAL HOSPITAL OF NANJING MILITARY REGION OF PLA, Nanjing (CN)

( * ) Notice: Subject to any disclaimer, the term of this patent is extended or adjusted under 35 U.S.C. 154(b) by 0 days.

(21) Appl. No.: 15/054,367

(22) Filed: Feb. 26, 2016

(30) Foreign Application Priority Data

Oct. 23, 2015 (CN) .......................... 2015 1 0698580

(51) Int. Cl.
*A61K 31/517* (2006.01)
*C07D 239/94* (2006.01)
*A61K 45/06* (2006.01)

(52) U.S. Cl.
CPC .......... *C07D 239/94* (2013.01); *A61K 31/517* (2013.01); *A61K 45/06* (2013.01)

(58) Field of Classification Search
None
See application file for complete search history.

(56) References Cited

U.S. PATENT DOCUMENTS

| 7,709,479 | B1 | 5/2010 | Mortlock et al. |
| 8,835,458 | B2 | 9/2014 | Bae et al. |
| 2013/0165386 | A1 | 6/2013 | Bae et al. |

FOREIGN PATENT DOCUMENTS

| WO | 96/09294 | 3/1996 |
| WO | 01/21596 | 3/2001 |
| WO | 2012/030160 | 3/2012 |

*Primary Examiner* — Craig Ricci
(74) *Attorney, Agent, or Firm* — Rankin, Hill & Clark LLP

(57) ABSTRACT

The invention discloses a novel quinazoline derivative LU1501 and a preparing method thereof, wherein the quinazoline derivative has a chemical name of N-[(4-fluorophenyl)methyl]-4-N-{7-methoxy-6-[(2-pyrrolidin-1-yl)hydroxyethyl]quinazoline-4-yl}phen-1,4-diamine. The quinazoline derivative and a pharmaceutically acceptable salt, a solvate and a hydrate thereof have excellent antitumor activity in vitro and in vivo to MCF-7, SK-BR-3, A549, HCT 116, U-118 MG; U-87 MG and MDA-MB-468, and have preferable application prospects on preparing anti-tumor drugs.

8 Claims, 1 Drawing Sheet

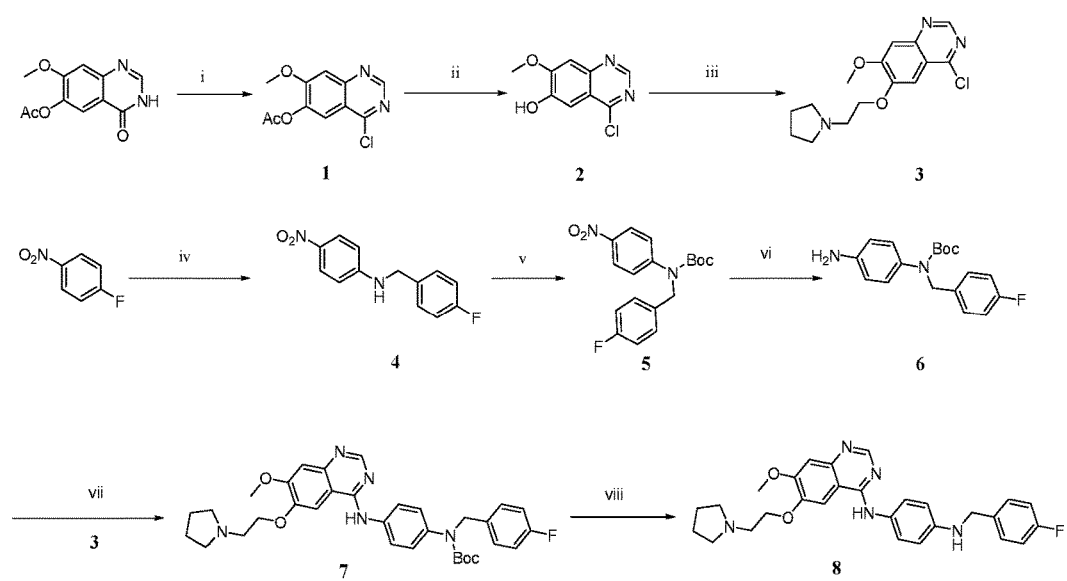

QUINAZOLINE DERIVATIVE LU1501 AND PREPARING METHOD AND APPLICATION THEREOF

TECHNICAL FIELD

The invention belongs to the field of biological medicines, and more particularly, relates to a novel quinazoline derivative Lu1501 and a preparing method and application thereof.

BACKGROUND

Malignant tumor is a common and frequently-occurring disease which severely threatens human's health. In recent 20 years, the tumor death rate in our country has been increased by 29.42%. Among the middle and prime aged crowds who are 35-59 years old, tumor has ranked the first among various causes of death. Data shows that the tumor incidence of our country is 200/100,000 people. In each year, there are about 2,200,000 or more newly-incident cases, and there are more than 6,000,000 patients receiving treatments. The treatment methods of tumor include operative treatment, radiotherapy and chemotherapy. At present, the chemotherapy is still the major means to treat tumor in clinic. One hotpot for new medicine study is to find out anti-tumor drugs. In recent years, 4-aminoquinazoline compounds have greatly drawn people's attention due to excellent biological activity thereof, and have become the researching hotpot of scholars from the biology and chemistry circles. The 4-aminoquinazoline compounds produce better inhibiting effects on EGF receptor or PDGF receptor tyrosine kinase, presenting such efficacy like resisting lung cancer, gastric cancer, colon cancer, breast cancer, gallbladder cancer, and prostatic cancer, and having effect like antibiosis, anti-HIV, anti-inflammation, and diabetes treatment, like those drugs on sale including gefitinib, erlotinib, lapatinib ditosylate, etc. It is found by the inventor that N-[(4-fluorophenyl)methyl]-4-N-{7-methoxy-6-[(2-pyrrolidin-1-yl)hydroxyethyl]quinazolin-4-yl}phen-1,4-diamine has certain anti-tumor activity. The inventor proposes an invention related to the N-[(4-fluorophenyl)methyl]-4-N-{7-methoxy-6-[(2-pyrrolidin-1-yl)hydroxyethyl]quinazolin-4-yl}phen-1,4-diamine or a pharmaceutically acceptable salt, a solvate or predrug thereof, or a stereoisomer or tautomer or metabolite thereof.

SUMMARY OF THE INVENTION

Object of the invention: in order to solve the problems in the prior art, the invention provides a novel quinazoline derivative LU1501, wherein the quinazoline derivative has a chemical name of N-[(4-fluorophenyl)methyl]-4-N-{7-methoxy-6-[(2-pyrrolidin-1-yl)hydroxyethyl]quinazoline-4-yl}phen-1,4-diamine, and has inhibitory activity on the proliferation of seven tumor cells including MCF-7, SK-BR-3, A549, HCT116, U-118 MG U-87 MG and MDA-MB-468.

Technical solution: in order to implement the above object, the invention provides a novel quinazoline derivative LU1501 which has a chemical name of N-[(4-fluorophenyl)methyl]-4-N-{7-methoxy-6-[(2-pyrrolidin-1-yl)hydroxyethyl]quinazoline-4-yl}phen-1,4-diamine, wherein the structural formula of the quinazoline derivative is as follows:

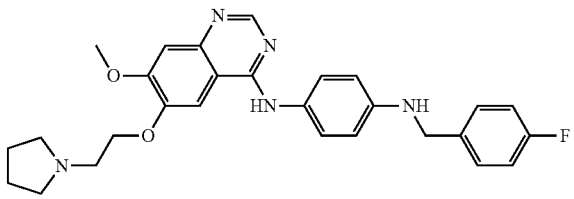 [SMILES: COc1cc2ncnc(Nc3ccc(NCc4ccc(F)cc4)cc3)c2cc1OCCN1CCCC1]

The invention further provides a preparing method for the above novel quinazoline derivative LU1501, which includes the following steps of:

S1: adding DMF to $SOCl_2$ dropwise slowly under the protection of nitrogen to catalyze, then adding 7-methoxy-4-oxo-3,4-dihydro-quinazolin-6-yl acetate, heating at 60-100° C. for 3-6 h, and reacting to generate a compound (1) which is namely 4-chloro-7-methoxy quinazolin-6-yl acetate;

S2: adding a solution of amino methanol dropwise slowly to the compound (1) while stirring in an ice bath, reacting for over 30 min while stirring when the reaction fluid is under 10° C., filtering, and washing a filter residue with diethylether, thus obtaining a reduced product compound (2) which is namely 4-chloro-7-methoxy quinazolin-6-ol;

S3: dissolving the compound (2), N-(2-hydroxyethyl) pyrrolidine, and $PPh_3$ in tetrahydrofuran under the protection of nitrogen, adding DTAD by batch while stirring in an ice bath, and reacting for over 6 h, thus generating a compound (3) which is namely 4-chloro-7-methoxy-6-[(2-pyrrolidin-1-yl)hydroxyethyl]quinazoline;

S4: dissolving 1-fluoro-4-nitrobenzene, 4-fluorophenyl methylamine and sodium carbonate with DMSO under the protection of argon, and reacting for 4-12 h with stirring at 100-120□, thus generating a compound (4) which is namely N-[(4-fluorophenyl)methyl]-4-nitroaniline;

S5: adding the compound (4) to $Boc_2O$ with dichloromethane as a solvent in an ice bathe under the protection of nitrogen, then adding DMAP to catalyze, reacting for 4-12 h with stirring, and performing secondary amine Boc protection, thus generating a compound (5) which is namely tert-butyl N-[(4-fluorophenyl)methyl]-N-(4-nitrophenyl) carbamate;

S6: dissolving the compound (5) in methanol, adding 10% Pd/C to catalyze, pumping in $H_2$, and reacting for 4-12 h with stirring to reduce to a compound (6) which is namely tert-butyl N-(4-aminophenyl)-N-[(4-fluorophenyl)methyl] carbamate;

S7: dissolving the compound (6) and the compound (3) in isopropanol, and reacting for 3-12 h at 80-100° C. under the catalysis of p-toluenesulfonic acid with stirring, thus generating a compound (7) which is namely tert-butyl N-[(4-fluorophenyl)methyl]-N-4-{7-methoxy-6-[(2-pyrrolidin-1-yl)hydroxyethyl]quinazolin-4-yl}aminophenyl carbamate; and S8: dissolving the compound (7) in a mixed solvent of dichloromethane/trifluoroacetic acid, and stirring at 25-45 □ for 1-6 h to remove Boc, thus generating a compound (8) which is namely N-[(4-fluorophenyl)methyl]-4-N-{7-methoxy-6-[(2-pyrrolidin-1-yl)hydroxyethyl]quinazolin-4-yl}phen-1,4-diamine.

Preferably, in step S1, the adding rate of DMF is 2-3 ml/min, and the dosage ratio of the $SOCl_2$ to the DMF to the 7-methoxy-4-oxo-3,4-dihydroquinazolin-6-yl acetate is 500-1000 mL to 10-20 mL to 100-150 g; and in step S2, the concentration of the $NH_3$-methanol solution is 7M, the adding rate of the $NH_3$-methanol solution is 3-10 ml/min, and the dosage of the $NH_3$-methanol solution being added to per gram compound (1) is 10-20 mL.

In step S3, the DTAD is added by 3-6 batches, with an interval of 2-4 h between each of the batches, wherein the dosage ratio by mole of the N-(2-hydroxyethyl)pyrrolidine to the PPh3 to the DTAD to compound (2) is 1 to 1 to 1 to 0.8-1.4.

In step S4, the dosage ratio by mole of the 1-fluoro-4-nitrobenzene to the 4-fluorophenyl methylamine to the sodium carbonate is 1 to 1 to 0.8-1.4.

In step S5, the compound (4) is added to $Boc_2O$ by 3-6 batches, with an interval of 5-10 min between each of the batches, wherein the dosage ratio by mole of the compound (4) to the $Boc_2O$ is 1 to 0.8-1.5, and the dosage ratio by mole of the compound (4) to the DMAP is 1 to 0.8-1.5.

In step S6, the amount of the 10% Pd/C being added to per 10 mmol compound (5) is 0.6-1.5 g.

In step S7, the dosage ratio by mole of the compound (6) to the compound (3) to the p-toluenesulfonic acid is 1 to 1 to 1.1-1.5.

In step S8, the mixed solvent of the dichloromethane/ trifluoroacetic acid is obtained by mixing dichloromethane and trifluoroacetic acid with a volume ratio of 2-5 to 1, and the dosage of the mixed solvent being added to per 1 g compound (7) is 10-20 mL.

The invention further provides an application of the novel quinazoline derivative in anti-tumor agent preparation.

The invention provides a pharmaceutical composition at the same time, wherein the pharmaceutical composition includes the compound and the pharmaceutically acceptable carrier according to claim 1.

Further, the invention provides a use of the compound or the pharmaceutical composition in drug preparation.

Meanwhile, the invention further provides an application of the novel quinazoline derivative LU1501 or the pharmaceutically acceptable salt, the solvate or prodrug thereof, or the stereoisomer or tautomer or metabolite thereof in anti-tumor agent preparation.

Finally, the invention provides an application of the novel quinazoline derivative LU1501 or the pharmaceutically acceptable salt, the solvate or prodrug thereof, or the stereoisomer or tautomer or metabolite combined with one or more anti-cancer agents in preparing medicine for treating tumor.

Beneficial effects: the invention discloses a novel quinazoline derivative LU1501, and employs an MTT method to evaluate the inhibitory activity thereof on the proliferation of seven tumor cells including MCF-7, SK-BR-3, A549, HCT116, U-118 MG U-87 MG and MDA-MB-468, and calculate the $IC_{50}$ value of the proliferation of the seven tumor cell. The result shows that the prepared novel quinazoline derivative LU1501 has inhibition effect on the above tumor cells, and can be used for preparing anti-tumor agents.

BRIEF DESCRIPTION OF THE DRAWINGS

FIG. 1 is a synthetic route diagram of quinazoline derivative, wherein i) $SOCl_2$, DMF; ii) $NH_3$/MeOH; iii) (N-(2-hydroxyethyl)pyrrolidine, $PPh_3$, DTAD, THF; iv) 4-fluorophenyl methylamine, $Na_2CO_3$, DMSO; v) $Boc_2O$, DMAP; vi) MeOH, $H_2$, Pd/C; vii) i-PrOH, TsOH; viii) DCM, TFA.

DETAILED DESCRIPTION OF THE PREFERRED EMBODIMENTS

In order to further describe the invention, a series of embodiments are given hereinafter. These embodiments are completely exemplary, which are only used to describe the invention in details, but should not be deemed as a limitation to the invention.

Embodiment 1 Prepare 4-chloro-7-methoxy quinazolin-6-yl acetate (Compound 1)

1000 mL sulfoxide chloride ($SOCl_2$) was added into 2000 mL nitrogen-protected four-neck round-bottom flask, 10 mL DMF was dropwise added slowly for catalyzing (dropwise added in 20 min), then 100 g 7-methoxy-4-oxo-3,4-dihydroquinazolin-6-yl acetate was added, and stirred for 3 h under 100□. The reaction fluid is cooled to room temperature in an ice bath, subjected to vacuum concentration, dried and then dissolved with 1000 mL dichloromethane, and then 1000 mL ice water was poured in. A mixture fluid was extracted by twice using dichloromethane to combine an organic layer, and then were washed by thrice using saturated aqueous sodium chloride solution. The organic layer was separated out and dried for 6 h in a 250 mL triangular flask by adding anhydrous sodium sulfate, then was subjected to vacuum filtration. The filtrate was subjected to vacuum concentration and dried, and washed by diethyl-ether, thus obtaining 65 g (yield 60%) compound 1, which was pale yellow powder.

Embodiment 2 Prepare 4-chloro-7-methoxy quinazolin-6-ol (Compound 2)

10 g 4-chloro-7-methoxy quinazolin-6-yl acetate (compound 1) was placed into a 250 mL three-neck round-bottom flask, 100 mL 7M $NH_3$-methanol solution was dropwise added while being stirred in an ice bath, and completely dropwise added in 30 min. The stirring reaction was performed for more than 30 min under 100. The reaction fluid was subjected to vacuum filtration, then a filtration residue was washed by twice using diethyl-ether, thus obtaining 6.5 g (yield 78%) compound 2, which was pale yellow powder.

Embodiment 3 Prepare 4-chloro-7-methoxy-6-[(2-pyrrolidin-1-yl)hydroxyethyl]quinazoline (Compound 3)

6.5 g 4-chloro-7-methoxy quinazolin-6-ol (compound 2), 4.6 g N-(2-hydroxyethyl)pyrrolidine, and 10.54 g $PPh_3$ were dissolved into 120 mL tetrahydrofuran, placed in a 250 mL nitrogen-protected three-neck round-bottom flask, and 9.25 g DTAD was added by three batches with an interval of 3 h/times under an ice bath, and stirred for 12 h under a room temperature. 100 mL water was added for terminating the reaction, and the reaction fluid was extracted by thrice using 200 mL dichloromethane to combine an organic layer, and then was washed by once using saturated aqueous sodium chloride solution. The organic layer was separated out and dried for 6 h in a 250 mL triangular flask by adding anhydrous sodium sulfate, then was subjected to vacuum filtration. The filtrate was subjected to vacuum concentration and dried, and then subjected to column chromatography, thus obtaining 4 g (yield 42%) compound 3, which was colorless powder.

Embodiment 4 Prepare N-[(4-fluorophenyl)methyl]-4-nitroaniline (Compound 4)

10 g 1-fluoro-4-nitrobenzene and 8.86 g 4-fluorophenyl methylamine were dissolved into 100 mL DMS, 22.6 g sodium carbonate was placed into a 250 mL nitrogen-protected three-neck flask, stirred for 12 h at 1000, and cooled to room temperature under an ice bath. 200 mL ice water was added into the reaction fluid, then vacuum filtration was performed, and the filtration residue was washed by 100 mL diethyl-ether, thus obtaining 12 g (yield 69%) compound 4, which was yellow powder.

Embodiment 5 Prepare tert-butyl N-[(4-fluorophenyl)methyl]-N-(4-nitrophenyl)carbamate (Compound 5)

3 g N-[(4-fluorophenyl)methyl]-4-nitroaniline (compound 4) and 4 g Boc$_2$O were dissolved into 100 mL dichloromethane, placed in a 250 mL nitrogen-protected three-neck flask, 2.23 g DMAP was added by three batches under an ice bath for catalyzing with an interval of 5 min/times, and stirred for 12 h under room temperature. 200 mL dichloromethane was supplementary added into a reaction fluid, washed by once using 100 mL 1M HCl solution, and washed by once using 100 mL saturated aqueous sodium chloride solution. A dichloromethane layer was separated out and dried for 6 h in a 250 mL triangular flask by adding anhydrous sodium sulfate, then was subjected to vacuum filtration. The filtrate was subjected to vacuum concentration and dried, and then subjected to column chromatography, thus obtaining 3.4 g (yield 81%) compound 5, which was colorless powder.

Embodiment 6 Prepare tert-butyl N-(4-aminophenyl)-N-[(4-fluorophenyl)methyl]carbamate (Compound 6)

3.4 g tert-butyl N-[(4-fluorophenyl)methyl]-N-(4-nitrophenyl)carbamate (compound 5) was dissolved in 100 mL methanol, placed in a 250 mL round-bottom flask, 1.5 g 10% palladium on carbon was added, and sufficient nitrogen was pumped in. The mixture was stirred for 12 h under room temperature, subjected to vacuum filtration, then the filtrate was concentrated and dried, thus obtaining 2.8 g (yield 90%) compound 6, which was yellow powder.

Embodiment 7 Prepare tert-butyl N-[(4-fluorophenyl)methyl]-N-4-{7-methoxy-6-[(2-pyrrolidin-1-hydroxyethyl]quinazolin-4-yl}aminophenyl carbamate (Compound 7)

1.46 g 4-chlor-7-methoxy-6-[(2-pyrrolidin-1-yl)hydroxyethyl]quinazoline (compound 3), 1.5 g tert-butyl N-(4-aminophenyl)-N-[(4-fluorophenyl)methyl]carbamate (compound 6), and 1.06 g p-toluenesulfonic acid were dissolved into 50 mL isopropanol, placed in a 100 mL nitrogen-protected three-neck flask, stirred for 3 h at 900, and then cooled to room temperature in an ice bath. The reaction fluid was subjected to vacuum concentration and dried, then subjected to column chromatography, thus obtaining 4 g (yield 33%) compound 7, which was yellow powder.

Embodiment 8 Prepare N-[(4-fluorophenyl)methyl]-4-N-{7-methoxy-6-[(2-pyrrolidin-1-yl)hydroxyethyl]quinazolin-4-yl}phen-1,4-diamine (Compound 8, i.e. LU1501)

4 g N-tert-butyl N-[(4-fluorophenyl)methyl]-N-4-{7-methoxy-6-[(2-pyrrolidin-1-hydroxyethyl]quinazolin-4-yl}aminophenyl carbamate (compound 7) was dissolved in 60 mL mixed solvent of dichloromethane/trifluoroacetic acid (2:1), placed in an 100 mL three-neck round-bottom flask, subjected to heating reflux, stirred for 2 h, and then cooled to room temperature in an ice bath. The reaction fluid was subjected to vacuum concentration and dried, then 100 mL dichloromethane was added to adjust the pH value to 9. The mixture fluid was extracted by thrice using dichloromethane to combine an organic layer, and then was washed by twice using saturated aqueous sodium chloride solution. A dichloromethane layer was separated out and dried for 6 h in a 250 mL triangular flask by adding anhydrous sodium sulfate, then was subjected to vacuum filtration. The filtrate was subjected to vacuum concentration and dried, and then subjected to column chromatography, thus obtaining 1.35 g (yield 41%) compound 8, which was yellow powder.

ESI-MS standard was conducted on the prepared compound 8, wherein the results were as follows:

ESI-MS(m/z): 488[M+H]+; $^1$H-NMR (300 MHz, CD$_3$Cl, ppm) δ 8.60 (s, 1H), 7.69-7.63 (m, 1H), 7.53-7.51 (m, 3H), 7.43-7.35 (m, 2H), 7.21 (s, 1H), 7.08-7.03 (t, J=8.4 Hz, 2H), 6.70-6.68 (d, J=8.7 Hz, 2H), 4.50-4.46 (t, J=6.0 Hz, 2H), 4.35-4.33 (m, 2H), 4.08-4.06 (m, 1H), 4.00 (s, 3H), 3.18-3.11 (t, J=5.7 Hz, 4H), 2.92-2.78 (m, 1H), 1.93-1.84 (m, 4H).

Embodiment 9 Evaluation of Inhibitory Activity of Compound 8 on the Proliferation of Tumor Cells (1) Tested Sample:
The compound 8 of the invention was prepared into required concentrations using a culture medium containing 0.1% DMSO.
(2) Cell Strain:
The seven tumor cells including MCF-7 (human breast cancer cell, ATCC:HTB-22), SK-BR-3 (human breast cancer cell, ATCC:HTB-30), A549 (human non-small cell lung cancer cell, ATCC:CRM-CCL-185), HCT116 (human colon cancer cell, ATCC:CCL-247), U-118 MG (human astrocytoma, ATCC:HTB-15), U-87 MG (human astrocytoma, ATCC:HTB-14), MDA-MB-468 (human breast cancer cell, ATCC:HTB-132) were all purchased from American Type Culture Collection (ATCC).
(3) Main Instruments and Materials
Ultrapure water purifier: MILLIPORE Direct-Q 3;
Autoclaves sterilizer: HVE-50, Hirayama Corporation;
Digital-display constant-temperature water bath: HH-4, Guohua Electric Appliances Co., Ltd.
Super clean bench: VS-1300-U clean bench, Suzhou Antai Airtech Co. Ltd.
Cell incubator: HF151UVCO2 incubator, Shanghai Lishen Corporation;
Refrigerated centrifuge: Shanghai Anting Scientific Instrument Plant
Microplate reader: ELx800, Biotek Corporation
Flat oscillator: ZD-9556, Taicang Science and Education Instrument Plant 96 hole cell culture plate, and 25 cm$^2$ culture bottle: Corning Costar Corporation;
2 mL freezing tube: Corning Costar Corporation;
(4) Major Reagents
RPMI-1640 culture medium: Gibco Corporation;
DMEM culture medium: Gibco Corporation;
L-15 culture medium: Gibco Corporation;
McCoy's 5A culture medium: Gibco Corporation;
MEM culture medium: Gibco Corporation;
PBS buffer solution: Gibco Corporation;
Fetal calf serum: Gibco Corporation;
0.25% pancreatin solution: Hyclone Corporation;

MTT (methylthiazo-letrazolium): Sigma Corporation, dissolved in PBS solution, and prepared into 5 mg/mL solution, used after being filtered and sterilized, and kept out of the sun;
Adriamycin amycin (ADR): Beijing Huafeng Union Technology Co., Ltd.
DMSO: dimethyl sulfoxide, Sigma Corporation;
(5) Test Method DMEM culture medium was selected for MCF-7 and U-118 MG cells, MEM culture medium was selected for U-87 MG cell, L-15 culture medium was selected for MDA-MB-468 cell, McCoy's 5A culture medium was selected for HCT 116 cell, and RPMI-1640 culture medium was selected for other cells. All the culture mediums contained 10% inactivated fetal calf serum, 80 $U \cdot mL^{-1}$ penicillin and 0.08 $mg \cdot mL^{-1}$ streptomycin.

MCF-7, SK-BR-3, A549, HCT 116, U-118 MG U-87 MG and MDA-MB-468 cells in logarithmic phase with excellent growth conditions were grafted into a 96-well plate according to a density of 1×104 cells/mL, wherein each well was grafted 100 μl. The cells were cultured for 12 h in 5% $CO_2$ incubator at 37° C. for adherence. A sterilized compound 8 to be tested and dissolved into the culture medium was added into the drugged cell holes according to a preset concentration gradient, wherein each hole was added 200 μl; and equal-volume culture medium was added into the blank cell holes, and equal-volume adriamycin amycin (ADR) dissolved in the culture medium was added according to the preset concentration gradient to the control cell holes, wherein 6 holes were parallel. After being cultured in the 5% $CO_2$ incubator at 37° C. for 48 h, 10 μl 5 mg/mL MTT solution was added in each hole, and then the mixture was continuously placed in the 5% $CO_2$ incubator at 37° C. for 4 h. A supernate was absorbed out carefully, 150 μl DMSO was added into each hole to dissolve purple residue (formazan), flatly oscillated for 10 min to completely dissolve deposits, then O.D. value (absorbancy) was measured on a microplate reader, wherein the wavelength was 570 nm.

The inhibition rates of the samples under each sample concentration on the tumor cells were calculated according to a formula that "relative survival rate=(D drug-containing–D blank)/(D control–D blank)×100%".

The test was repeated for thrice. A diagram was made by plotting the inhibition rate against the concentration of the compound, and the $IC_{50}$ (half effective inhibitive concentration) value of the compound 8 of the invention was calculated. Meanwhile, adriamycin amycin (ADR) was employed as a control positive drug.
(6) Test Result

The invention claimed is:
1. A method for preparing a quinazoline derivative comprising the following steps of:
S1: adding DMF to $SOCl_2$ dropwise slowly under the protection of nitrogen to catalyze, then adding 7-methoxy-4-oxo-3,4-dihydroquinazolin-6-yl acetate, heating at 60-100° C. for 3-6 h, and reacting to generate a compound (1) which is 4-chloro-7-methoxy quinazolin-6-yl acetate;
S2: adding $NH_3$-methanol solution dropwise slowly to the compound (1) while stirring in an ice bath, reacting for over 30 min while stirring when the reaction fluid is under 10° C., filtering, and washing a filter residue with diethyl-ether, thus obtaining a reduced product compound (2) which is 4-chloro-7-methoxy quinazolin-6-ol;
S3: dissolving the compound (2), N-(2-hydroxyethyl) pyrrolidine, and $PPh_3$ in tetrahydrofuran under the protection of nitrogen, adding DTAD while stirring in an ice bath, and reacting for over 6 h, thus generating a compound (3) which is 4-chloro-7-methoxy-6-[(2-pyrrolidin-1-yl)hydroxyethyl]quinazoline;
S4: dissolving 1-fluoro-4-nitrobenzene, 4-fluorophenyl methylamine and sodium carbonate with DMSO under the protection of argon, and reacting for 4-12 h with stirring at 100-120° C., thus generating a compound (4) which is N-[(4-fluorophenyl)methyl]-4-nitroaniline;
S5: adding the compound (4) to $Boc_2O$ with dichloromethane as a solvent in an ice bath under the protection of nitrogen, then adding DMAP to catalyze, reacting for 4-12 h with stirring, and performing secondary amine Boc protection, thus generating a compound (5) which is tert-butyl N-[(4-fluorophenyl)methyl]-N-(4-nitrophenyl)carbamate;
S6: dissolving the compound (5) in methanol, adding 10% Pd/C to catalyze, pumping in $H_2$, and reacting for 4-12 h with stirring to reduce to a compound (6) which is tert-butyl N-(4-aminophenyl)-N-[(4-fluorophenyl)methyl]carbamate;
S7: dissolving the compound (6) and the compound (3) in isopropanol, and reacting for 3-12 h at 80-100° C. under the catalysis of p-toluenesulfonic acid with stirring, thus generating a compound (7) which is tert-butyl N-[(4-fluorophenyl)methyl]-N-4-{7-methoxy-6-[(2-pyrrolidin-1-hydroxyethyl]quinazolin-4-yl}aminophenyl carbamate; and
S8: dissolving the compound (7) in a mixed solvent of dichloromethane/trifluoroacetic acid, and stirring at 25-45° C. for 1-6 h to remove Boc, thus generating a quinazoline derivative of compound (8) which is N-[(4-

TABLE 1

Inhibitory Activity of Compound 8 LU1501 on the Proliferation of Tumor Cells ($IC_{50}$ ± SD μM)

| Compound | MCF-7 | SK-BR-3 | A549 | HCT 116 | U-118 MG | U-87 MG | MDA-MB-468 |
|---|---|---|---|---|---|---|---|
| ADR | 3.98 ± 0.07 | 4.65 ± 0.02 | 0.58 ± 0.05 | 26.57 ± 0.12 | 13.49 ± 1.75 | 82.47 ± 7.15 | 2.45 ± 0.31 |
| Compound 8 | 16.13 ± 3.47 | 10.16 ± 0.86 | 5.66 ± 1.01 | 2.90 ± 1.02 | 24.48 ± 2.68 | 5.45 ± 0.61 | 19.45 ± 1.33 |

As shown in FIG. 1, the test result of the inhibitory activity of compound 8 on the proliferation of tumor cells was given, wherein the result indicated that the novel quinazoline derivative prepared had certain inhibition effect on the above tumor cells, and may be used to prepare anti-tumor agents.

fluorophenyl)methyl]-4-N-{7-methoxy-6-[(2-pyrrolidin-1-yl)hydroxyethyl]quinazolin-4-yl}phen-1,4-diamine.
2. The method according to claim 1, wherein in step S1, the adding rate of DMF is 2-3 ml/min, and the dosage ratio of the $SOCl_2$ to the DMF to the 7-methoxy-4-oxo-3,4-dihydroquinazolin-6-yl acetate is 500-1000 mL to 10-20 mL to 100-150 g; and in step S2, the concentration of the NH$_3$-methanol solution is 7M, the adding rate of the NH$_3$-methanol solution is 3-10 ml/min, and 10-20 mL of the NH$_3$-methanol solution is added per gram of the compound (1).

3. The method according to claim 1, wherein in step S3, the DTAD is added in 3-6 batches, with an interval of 2-4 h between adding each of the batches of the DTAD, wherein the dosage ratio by mole of the N-(2-hydroxyethyl)pyrrolidine to the PPh$_3$ to the DTAD to compound (2) is 1 to 1 to 1 to 0.8-1.4.

4. The method according to claim 1, wherein in step S4, the dosage ratio by mole of the 1-fluoro-4-nitrobenzene to the 4-fluorophenyl methylamine to the sodium carbonate is 1 to 1 to 0.8-1.4.

5. The method according to claim 1, wherein in step S5, the compound (4) is added in 3-6 batches to Boc$_2$O, with an interval of 5-10 min between adding each of the batches of the compound (4), wherein the dosage ratio by mole of the compound (4) to the Boc$_2$O is 1 to 0.8-1.5, and the dosage ratio by mole of the compound (4) to the DMAP is 1 to 0.8-1.5.

6. The method according to claim 1, wherein in step S6, 0.6-1.5 g of the 10% Pd/C is added per 10 mmol of the compound (5).

7. The method according to claim 1, wherein in step S7, the dosage ratio by mole of the compound (6) to the compound (3) to the p-toluenesulfonic acid is 1 to 1 to 1.1-1.5.

8. The method according to claim 1, wherein in step S8, the mixed solvent of the dichloromethane/trifluoroacetic acid is obtained by mixing dichloromethane and trifluoroacetic acid with a volume ratio of 2-5 to 1, and 10-20 mL of the mixed solvent is added per 1 g compound (7).

* * * * *